United States Patent [19]

Nishikawa et al.

[11] 4,101,378

[45] * Jul. 18, 1978

[54] PROCESS FOR THE MICROBIOLOGICAL OXIDATION OF STEROIDS

[75] Inventors: Daikichiro Nishikawa, Tokyo; Yukio Imada; Masayuki Kinoshita, both of Yokohama; Katsuhiko Takahashi, Kawasaki; Hajime Machida, Tokyo; Michitaro Nagasawa, Noda, all of Japan

[73] Assignees: Mitsubishi Chemical Industries Limited, Tokyo; Noda Institute for Scientific Research, Chiba, both of Japan

[*] Notice: The portion of the term of this patent subsequent to Nov. 15, 1994, has been disclaimed.

[21] Appl. No.: 824,902

[22] Filed: Aug. 15, 1977

Related U.S. Application Data

[62] Division of Ser. No. 693,685, Jun. 7, 1976, Pat. No. 4,057,469.

[30] Foreign Application Priority Data

Jun. 6, 1975 [JP] Japan .................................. 50-68379
Sep. 22, 1975 [JP] Japan ................................ 50-114431

[51] Int. Cl.² ............................................ C07B 29/02
[52] U.S. Cl. .................................................. 195/51 G
[58] Field of Search ...................................... 195/51 G

[56] References Cited

U.S. PATENT DOCUMENTS

| 2,756,179 | 7/1956 | Fried et al. | 195/51 E |
|---|---|---|---|
| 3,388,042 | 6/1968 | Arima et al. | 195/51 G |
| 3,684,656 | 8/1972 | Waard | 195/51 G |
| 3,684,657 | 8/1972 | Krachy et al. | 195/51 G |

FOREIGN PATENT DOCUMENTS 16,147  1971  Japan ................................ 195/51 R

OTHER PUBLICATIONS

Rose, Industrial Microbiology, p. 273 (1961).

*Primary Examiner*—Alvin E. Tanenholtz
*Attorney, Agent, or Firm*—Oblon, Fisher, Spivak, McClelland & Maier

[57] ABSTRACT

The improvement in a process for the production of 17-hydroxyandrosta-1,4-dien-3-one and androsta-1,4-diene-3,17-dione by the microbiological oxidation of a sterol, its 4-en-3-one derivative or its 1,4-dien-3-one derivative, which comprises adding to the culture medium at least one glyceride-containing substance selected from the group consisting of glycerides, fats, oil seeds and oil fruits in an amount sufficient that the culture medium contains at least 0.3 percent by weight of glycerides.

19 Claims, 1 Drawing Figure

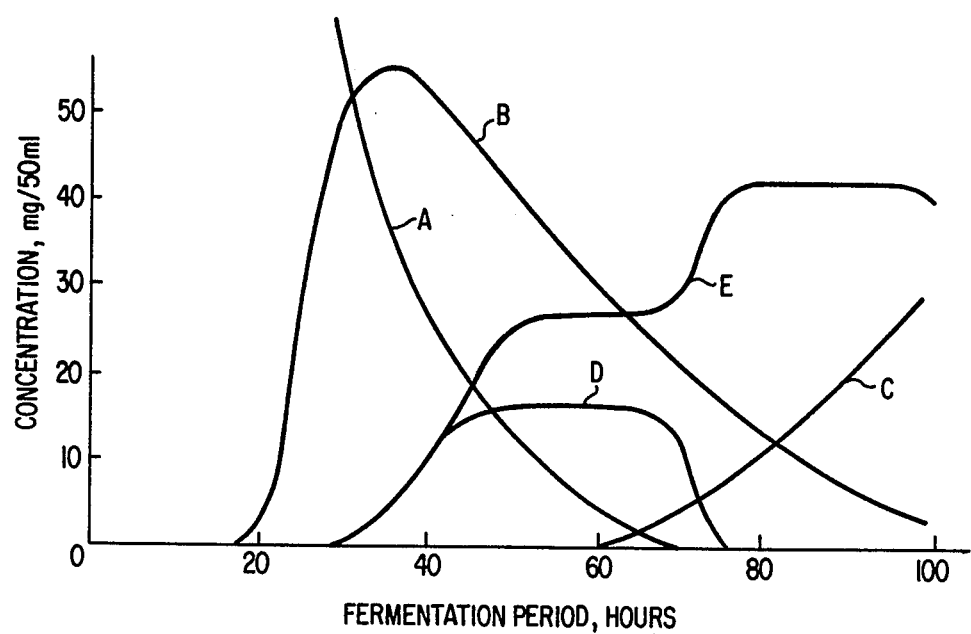

PROCESS FOR THE MICROBIOLOGICAL OXIDATION OF STEROIDS

This is a division, of application Ser. No. 693,685 filed June 7, 1976 now U.S. Pat. No. 4,057,469.

BACKGROUND OF THE INVENTION

1. Field of the Invention

This invention relates to an improved process for the production of 17-hydroxyandrosta-1,4-dien-3-one and androsta-1,4-diene-3,17-dione by the microbiological oxidation of a sterol, its 4-en-3-one derivative or its 1,4-dien-3-one derivative.

2. Description of the Prior Art

17-Hydroxyandrosta-1,4-diene-3-one and androsta-1,4-diene-3,17-dione are commercially significant intermediates for the synthesis of valuable steroidal hormones. It has long been known that 17-hydroxyandrosta-1,4-dien-3-one (1-dehydrotestosterone) (hereinafter referred to as DHT) and androsta-1,4-diene-3,17-dione (hereinafter referred to as ADD) are formed by the microbiological oxidation of sterols. However, this process suffers from the disadvantage that the formed DHT and ADD are subject to further oxidation which results in poor yields of DHT and ADD. U.S. Pat. No. 3,388,042 to Arima et al., issued June 11, 1968, discloses the microbiological oxidation of sterols to ADD through the use of a chelating agent capable of forming chelate compounds with iron and copper ions which are present in the culture medium and which participate in the microbiological oxidation of ADD. Although this process permits the avoidance of the further oxidation of ADD to give excellent results, it has not achieved commercially attractive yields and conversions. Therefore, improvement in the process was required to improve such yields and conversions.

It is well known that media containing fats and oils are employed in the microbiological oxidation of steroids. U.S. Pat. No. 2,756,179 to Josef Fried et al., issued July 24, 1956, describes in Example 1 the use of a medium containing about 0.22 percent by weight of soybean oil and about 1.5 percent by weight of soybean meal in the microbiological oxidation of progesterone to ADD and DHT. U.S. Pat. No. 2,842,566 to Jean P. Rosselet et al., issued July 8, 1958, describes in Example 1 the use of a medium containing about 0.1 percent by weight of lard oil in the microbiological oxidation of 6α-methyl-11-ketoprogesterone to 1-dehydro-6α-methyladrenosterone and 1-dehydro-6α-methyl-11-ketotestosterone. U.S. Pat. No. 2,981,659 to Gunther S. Fonken et al., issued Apr. 25, 1961, describes in Example 4A the use of a medium containing about 1.5 percent by weight of soybean meal and about 0.25 percent by weight of soybean oil in the microbiological oxidation of progesterone 20-ethylene ketal to 1-dehydroprogesterone 20-ethylene ketal. It also describes in Example 5A the use of a medium containing about 0.22 percent by weight of soybean oil or about 0.2 percent by weight of lard oil in the microbiological oxidation of progesterone 20-ethylene ketal to 1-dehydroprogesterone 20-ethylene ketal. U.S. Pat. No. 3,010,876 to Dan J. Badia et al., issued Nov. 28, 1961, describes in Example III the use of a medium containing about 0.27 percent by weight (10 ml./gal.) of soybean oil in the microbiological oxidation of Compound S to Compound F. U.S. Pat. No. 3,047,469 to Charles John Sih et al., issued July 31, 1962 discloses the use of a medium containing about 0.22 percent by weight of soybean oil in dehydrogenating the A ring of steroids having A rings which are fully or partially saturated in that ring. U.S. Pat. No. 3,536,586 to Bong Kuk Lee et al., issued Oct. 27, 1970, discloses the use of a medium containing about 0.22 percent by weight of soybean oil and about 1.5 to 2.0 percent by weight of soybean meal in 1-dehydrogenating and 16-hydroxylating a steroid which is saturated in the 1,2-position and which has a replaceable hydrogen atom in the 16-position. Japanese Patent published 16147/1971 describes in Example 4 the use of a medium containing about 0.1 percent by weight of soybean oil in the microbiological oxidation of cholesterol to ADD and androst-4ene-3,17-dione. Japanese Patent published 29193/1971 describes in Example 1 the use of a medium containing 0.2 percent by weight of soybean oil in the microbiological oxidation of lithocholic acid to ADD and androst-4-ene-3,17-dione. Biotechnology and Bioengineering 11 1255–1270 (1969) discloses the use of a medium containing about 0.22 percent by weight of soybean oil and about 1.5 to 2.0 percent by weight of soybean oil meal in the microbiological oxidation of 9α-fluoro-11β,17,21-trihydroxy-pregn-4-ene-3,20-dione-21-acetate to 9α-fluoro-11β,16α,17,21-tetrahydroxy-pregna-1,4-diene-3,20-dione.

However, the addition of such a small amount of the fat to the culture medium in the microbiological oxidation of sterols results in a slight increase in the yields of DHT and ADD.

SUMMARY OF THE INVENTION

It has now been discovered that when at least one glyceride-containing substance selected from the group consisting of glycerides, fats, oil seeds and oil fruits is added to the culture medium in an amount sufficient that the culture medium contains at least 0.3 percent by weight of glycerides, DHT and ADD are obtained at high yields and concentrations.

BRIEF DESCRIPTION OF THE DRAWING

The drawing is a plot of the concentration (mg/50 ml) of cholesterol (line A), cholest-4-en-3-one (line B) chlesta-1,4-dien-3-one (line C), DHT (line D) and ADD (line E) as ordinate against the fermentation period (hours) as abscissa.

DESCRIPTION OF THE PREFERRED EMBODIMENTS

As stated above, this invention is directed to the microbiological oxidation of a sterol, its 4-en-3-one derivative or its 1,4-dien-3-one derivative to DHT and ADD.

Although the process whereby the microbiological oxidation of sterols takes place is not fully understood, it is believed that the microbiological oxidation of sterols proceeds as follows: (see U.S. Pat. No. 3,388,042)

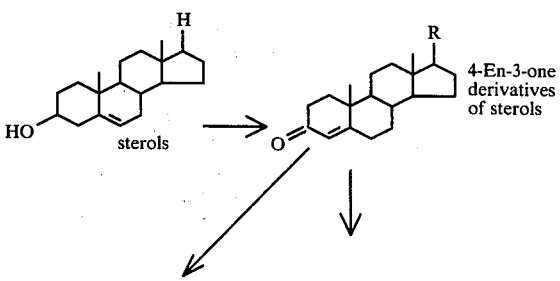

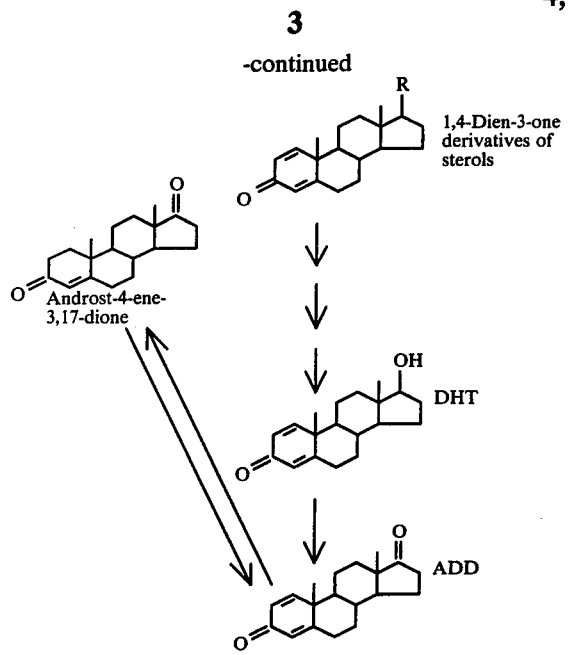

In the above formulas, R represents a side chain of 8 to 10 carbon atoms. The steroid substrates for the process of this invention are sterols, their 4-en-3-one derivatives and their 1,4-dien-3-one derivatives.

Sterols possess a hydroxy group at C-3, a double bond at C-5, a side chain of 8 to 10 carbon atoms at C-17, and in some cases, a double bond at C-7 of the perhydrocyclopentanophenanthrene nucleus.

Examples of such sterols are cholesterol, stigmasterol, campesterol, sitosterol, ergosterol, brassicasterol and fucosterol. Especially preferred are cholesterol, stigmasterol, campesterol and sitosterol.

It goes without saying that the 4-en-3-one derivatives and 1,4-dien-3-one derivatives of the sterols which are the intermediate oxidation products proposed in the above-described oxidation path of the sterols can also be employed as the starting materials of this invention. The concentration of the steroid substrate in the culture medium is not critical, and is generally in the range of from about 0.05 to about 5 weight percent, perferably in the range of from about 0.1 to about 3 weight percent. In accordance with the process of this invention, there is added to the culture medium at least one glyceride-containing substance selected from the group consisting of glycerides, fats, oil seeds and oil fruits. The glycerides which are added to the culture medium include monoglycerides, diglycerides and triglycerides. Likewise, single glycerides containing identical fatty acid residues, and mixed glycerides containing two or three different fatty and residues can also be employed. The fatty acid residues include unsaturated fatty acid residues and saturated fatty acid residues.

From the hyrophilic viewpoint, it is preferred that the fatty acid residue contains up to 26 carbon atoms.

Examples of suitable single glycerides are monoglycerides such as α-monoacetin, β-monoacetin, α-monopalmitin, β-monopalmitin, α-monostearin, β-monostearin, α-monoolein, β-monoolein and the like; diglycerides such as α,α'-diacetin, α,β-diacetin, α,α'λ dipalmitin, α,β-dipalmitin, α,α'distearin, α,α'-distearia, α,α'-diolein, α,β-diolein and the like: and triglycerides such as triacetin, trilaurin, trimyristin, tripalmitin, tristearin, triolein and the like.

Examples of suitable mixed glycerides are 1-aceto-2,3-dipalmitin, 1-palmito-2,3-dicaprin, 1-lauro-2-milisto-3-palmitin, 2-oleo-1,3-dipalmitin and 2-stearo-1,3-diolein. In the process of this invention, fats can be used in place of the glycerides. As used hereinabove, and as will be used hereinafter and in the claims, the term "fats" is intended to include vegetable fats and oils, and animal fats and oils regardless of their physical state.

Examples of suitable fats of plant origin are linseed oil, perilla oil, tung oil, sesame oil, corn oil, rapeseed oil, cottonseed oil, safflower oil, soybean oil, soya lecithin, camellia oil, rice bran oil, olive oil, castor oil, peanut oil, coconut oil, palm oil and palm kernel oil.

Cottonseed oil, soybean oil, rapeseed oil, palm oil and palm kernel oil are especially preferred due to their stable supply.

Examples of suitable fats of animal origin are fish oil, whale oil, beef tallow, lard, mutton tallow, beef foot oil and liver oil.

Especially preferred are lard, fish oil and whale oil. Likewise, glyceride-containing oil seeds or oil fruits can also be used in place of the glycerides.

As used hereinabove, and as will be used hereinafter and in the claims, the term "oil seeds and oil fruits" is intended to include fat-bearing seeds and fruits.

Examples of suitable oil seeds and oil fruits are linseed, olive, sesame, rapeseed, cottonseed, soybean, peanut and rice bran.

It is preferred that the oil seed and oil fruit be ground to a degree of fineness such that they are well assimilated. The glyceride-containing substance which is selected from the group consisting of glycerides, fats, oil seeds and oil fruits may be used individually, or if desired a mixture of two or more individual glyceride-containing substances may be employed.

The glyceride-containing substance is added to the culture medium in such an amount that the culture medium contains from 0.3 to 4.0 percent of glycerides, preferably from 0.5 to 3.5 percent of glycerides, more preferably from 0.7 to 3.0 percent of glycerides, each based on the weight of the culture medium.

The amount of the fats to be added will be calculated on the basis of the glyceride content of the fats. However, the main component of fats is glycerides, and accordingly, the weight of the fats is nearly equal to that of the glycerides.

Likewise, the amount of the glyceride-containing oil seeds or oil fruits to be added will be calculated on the basis of the glyceride content of the oil seeds or oil fruits. For reference, the glyceride contents of typical oil seeds and oil fruits are shown in the following table.

| Oil Seed or Oil Fruit | Glyceride Content (weight percent) |
|---|---|
| Olive (fruit) | 40–70 |
| Soybean | 15–23 |
| Cottonseed | 16–35 |
| Corn | 4–6 |
| Sesame | 35–56 |
| Rapeseed | 22–50 |
| Peanut | 29–39 |
| Camellia | 35 |
| Palm | 51–67 |
| Coconut | 65–75 |

The addition of vegetable oil meals along with the glyceride-containing substance to the culture medium has an especially beneficial effect on the production of DHT and ADD, and increases the yields of DHT and ADD considerably.

As used hereinabove, and as will be used hereinafter and in the claims, the term "vegetable oil meals" is intended to include refuses of vegetable fats and oils, which are the crushed residue from the extraction of oil-bearing seeds or fruits. Depending upon the extractive process, varying percentages of protein and fats will remain in the meals. However, any vegetable oil meals may be employed. In general, commercially available vegetable oil meals are preferred. Examples of suitable vegetable oil meals are soybeam oil meal, linseed oil meal, rapeseed oil meal, cottonseed meal, sesame oil meal, peanut oil meal and safflower oil meal The amount of the vegetable oil meal to be added varies widely with the amount of the glyceride--containing substance to be used, and is generally in the range of from about 0.1 to about 50 times the weight of the glyceride-containing substance, preferably from about 0.3 to about 30 times, and more preferably from about 0.6 to about 20 times the weight of the glyceride-containing substance. However, the concentration of the vegetable oil meal in the culture medium in normally in the range of about 0.3 to about 15 percent, preferably from about 0.6 to about 10 percent, and more preferably from about 1 to about 8 percent, each based on the weight of the culture medium. The addition of a larger amount of the glyceride-containing substance requires the selection of suitable microorganisms capable of assimilating glycerides well. In fact, the use of a microorganism which assimilates glycerides to a lower extent results in almost no occurence of the microbiological oxidation, because glycerides are not well assimilated and, at the same time, the glycerides become massive. Accordingly, the microorganism which can be used in the process of this invention is required to be capable of assimilating sterols and glycerides to a higher extent. Examples of such microorganisms are those belonging to

*Arthrobacter, Nocardia, Fusarium, Microbacterium, Mycobacterium, Protaminobacter, Brevibacterium, Corynebacterium, Bacillus, Serratia, Azotobacter Streptomyces, Alkaligenes* and *Pseudomonos.*

Representative of the above microorganisms are

*Arthrobacter simplex* (IAM 1660).
*Brevibacterium lipolyticum* (IAM 1398),
*Mycobacterium smegmatis* (IFO 3083),
*Protaminobacter alboflavus* (ATCC 8458),
*Nocardia erythropolis* (ATCC 4277),
*Corynebacterium equi* (IAM 1038) and
*Mycobacterium phlei* (IFO 3158).

Especially, preferred are *Arthrobacter simplex* and

*Brevibacterium lipolyticum*. As used hereinabove, and as will be used hereinafter, the term "IAM" refers to Institute of Applied Microbiology, Tokyo University, Tokyo, Japan, and the term "IFO" refers to Institute for Fermentation, Osaka, Osaka, Japan. The process of this invention is not limited to the above-listed microorganisms. A mixture of two or more of the above microorganisms may also be employed. In addition to the glyceride-containing substance and the vegetable oil meal, carbon sources, nitrogen sources and inorganic substances are incorporated in the culture medium. Examples of such carbon sources are hydrocarbon such as $\eta$-paraffins, $\alpha$-olefins, xylene and the like; alcohols such as methanol, ethanol, glycerol, higher alcohols and the like; organic acids such as succinic acid, acetic acid, higher fatty acids and the like, and the salt thereof; and saccharides such as starch, maltose, sucrose, glucose, rhamnose and the like. Natural nutrient sources containing carbon sources, nitrogen sources and other nutrient substances may be incorporated in the culture medium. Examples of such natural nutrient sources are molasses including hightest molasses, refinery molasses and xylose molasses; bagasse, corn cob, alfalfa, corn steep liquor, distillers'solubles, micki (an aqueous solution of amino acids mixture prepared by the hydrolysis of soybean oil meal with HCl), fish meal, yeast, bran, meat extract, yeast extract, potato extract, malt extract, gluten, peptone, glutamades, asparagine, glycine, cascin, casein hydrolysate and skimmed milk. Examples of the suitable inorganic substances which are incorporated in the culture medium are nitrogen sources such as ammonium sulfate, ammonium chloride and the like; potassium and phosphorus sources such as dipotassium hydrogenphosphate; and salts of iron, copper, magnesium, cobalt, zinc, calcium and the like.

Other components, e.g., vitamins, can be present in the culture medium if they do not impede the function of the main components.

The composition of the culture medium depends on the microorganism which is used. Carbon sources, nitrogen sources, potassium, phosphorus and magnesium are critical as components in the culture medium.

An anti-foaming agent, e.g., polyoxyalkylene glycol, may be incorporated in the culture medium, if necessary.

However, it need not always be added, since the glyceride-containing substance acts as an anti-foaming agent.

The culture medium can contain a surface active agent. This is not required, but does normally render the culture medium more conducive to manipulation.

Examples of the suitable surface active agents are polyoxyethylene sorbitan monostearate, sorbitan monopalmitate and polyethylene glycol monostearate.

In order to obtain DHT and ADD in high yields, it is necessary to add to the culture medium an inhibitor for the oxidation of DHT and ADD.

Examples of such inhibitors are nickel and cobalt salts, and chelating agents capable of forming chelate compounds with iron and copper ions. Representative of such chelating agents are 1,10-phenanthroline, 2,2'-bipyridyl, 8-hydroxyquinoline, cupferron, isonicotinic acid hydrazide, o-phenylenediamine and sodium N,N'-diethyl-dithiocarbamate. Especially preferred are 1,10-phenanthroline, 2,2'-bipyridyl and 8-hydroxyquinoline.

The concentration of the chelating agent in the culture medium varies widely with the nature of the chelating agent and the composition of the culture medium. In general, it is in the range of from about $1 \times 10^{-5}$ to about $1 \times 10^{-2}$M.

The time at which the chelating agent is added to the culture medium varies with the microorganism employed and the composition of the culture medium. In general, it is added at the end of a period of from 10 to 60 hours from the time of initiating the incubation.

The incubation temperature is normally in the range of from about 20° C to about 37° C.

When a microorganism belonging to the genus *Arthrobacter* or the genus *Brevibacterium* is employed, the preferred incubation temperature is about 30° C. When a microorganism belonging to the genus *Mycobacterium* is employed, the preferred incubation temperature is about 35° C.

It is desirable that the initial pH of the culture medium be between pH 5 and pH 8, and preferably about pH 7.

The steroid substrate, after sterilization by dry heat or wet heat, is added in any suitable manner, such as in the form of a powder or a solution in a suitable solvent, e.g., dimethylformamide, or in the form of a suspension prepared by ultrasonically dispersing it.

It is preferred that the steroid substrate and the surface active agent be simultaneously added because of the increased emulsification of the steroid substrate.

The time at which the steroid substrate is added to the culture medium varies with the microorganism used and the nature of the steroid substrate.

In general, the steroid substrate is added within 30 hours from the time of initiating the incubation. When the microorganism does not grow well, the steroid substrate may be added after 30 hours from the time of initiating the incubation. It is also possible to add the steroid substrate in portions, depending upon the growth of the microorganism.

Because the glyceride-containing substance and the vegetable oil meal which are added to the culture medium in accordance with the process of this invention are effective in stimulating the growth of the microorganism at all stages in the microbiological oxidation, they are generally added at the time of initiating the incubation.

It is believed that the glyceride-containing substance and the vegetable oil meal are especially effective in the oxidation of a side chain at C-17 of the steroid. Accordingly, the addition of the glyceride-containing substance and the vegetable oil meal at the time of the addition of the steroid substrate or within about 50 hours from the time of the addition of the steroid substrate increases the yields of DHT and ADD considerably.

It is also preferred to add the glyceride-containing substance in portions during the course of the fermentation to give the final concentration within the range described above, because it acts as an anti-forming agent as stated above. The term "the final concentration" as used herein is defined as the concentration of the total glycerides contained in the added glyceride-containing substance in the culture medium, although the glycerides decrease during the fermentation as a result of assimilation.

According to the process of this invention, DHT and ADD are obtained. In view of the proposed mechanism for the oxidation of the sterols as set forth herein above, it is believed that ADD is formed by the oxidation of the hydroxy group at C-17 of DHT. In fact, as shown in the attached drawing, the concentration of DHT which is higher at an early stage in the incubation decreases as the oxidation of the steroid substrate proceeds and, at the same time, the concentration of ADD increases. It follows from the above that, in order to attain a higher concentration of DHT, the incubation should be terminated at an early stage in the oxidation, whereas, in order to attain a higher concentration of ADD, the incubation should be continued for a long period of time.

The incubation time required for obtaining DHT or ADD at a higher concentration varies widely with the microorganism, the incubation temperature and the composition of the culture medium. In order to attain a higher concentration of DHT, it is preferred to terminate the incubation at the end of a period of from about 15 to about 35 hours from the time of the addition of the chelating agent, whereas, in order to attain a higher concentration of ADD, it is preferred to terminate the incubation at the end of a period of from about 35 to about 90 hours from the time of the addition of the chelating agent.

Upon completion of the fermentation, the resulting DHT and ADD are recovered from the fermentation broth by conventional methods. An especially advantageous method of recovering the products involves extracting the fermentation broth with a water-immiscible organic solvent, such as methylene chloride, chloroform, ether, benzene, toluene, ethyl acetate or the like.

After evaporation of the combined organic extracts, the resultant products can be purified by recrystallization from a suitable solvent, e.g., cyclohexane or by reprecipitation from a suitable combination of solvents, e.g., xylene-hexane.

Alternatively, the products can be chromatographed over a column packed with silica or alumina to obtain the separated individual products in substantially pure form. Eluents such as petroleum ether, benzene, chloroform, ether, methanol and the like can be employed. The separated products as obtained from the chromatographic procedure may be further purified by recrystalization from a suitable solvent.

Having generally described this invention, a more complete understanding can be obtained by reference to certain examples which are provided herein for purposes of illustration only are not intended to be limiting in any manner. In the following examples, analysis of the products is made by gas chromatography and the percentages are expressed in terms of area. Unless otherwise stated, the percentages in the following examples are by weight.

EXAMPLE 1

This Example illustrates the effect of the amount of cottonseed oil to be added on the yield of ADD.

A seed medium having the following composition is prepared:
 1.0 percent of yeast extract,
 1.0 percent of meat extract,
 1.0 percent of peptone, and
 remainder - water The pH of the seed medium was adjusted to 7.0 with NaOH. To a 500 ml shaker flask is added 100 ml of the seed medium. The flask and its contents are sterilized by autoclaving for a period of 15 minutes at a temperature of 120° C, and then cooled. The medium is inoculated with a loopful of *Arthrobacter simplex* (IAM 1660) and the inoculated medium is incubated for a period of 48 hours at a temperature of 28° C on a reciprocal shaker having a 7-cm stroke at 130 strokes per minute.

A main fermentation medium having the same composition as that of the seed medium with the exception that the required amount of cottonseed oil shown in Table 1 is added to the medium to achieve the listed concentration. The pH of the main fermentation medium is adjusted to 7.0 with NaOH. To a 500 ml shaker flask is added 50 ml of the main fermentation medium. The flask and its contents are sterilized by authoclaving for a period of 20 minutes at a temperature of 120° C, and then cooled. The flask is inoculated with 2 ml of the seed culture broth obtained above and then incubated at a temperature of 30° C on a reciprocal shaker having a 7-cm stroke at 130 strokes per minute.

At the end of 20 hours from the time of initating the incubation, 150 mg of cholesterol suspended in 2 ml of water is added. At the end of 28 hours from the time of initiating the incubation, 4.0 mg of 2,2'-bipyridyl is added. At the end of 85 hours from the time of the addition of 2,2'-bipyridyl, the incubation is stopped. The fermentation broth is extracted with 150 ml of ethyl acetate. The extract is concentrated, chromatographed on silica gel and eluted with benzene-acetone (1:1), thereby separating ADD from intermediate oxidation products and the steroid substrate. The yield of ADD is shown in Table 1.

Employing a mixture of β-sitosterol and campesterol (2:1), stigmasterol, cholest-4-en-3-one or cholesta-1,4-dien-3-one in place of cholesterol, the above described incubation is repeated.

In addition, the above-described incubation is repeated except that cottonseed oil is not added.

The results are shown together in Table 1.

TABLE 1

| Run No. | Substrate | Concentration of Cottonseed oil (Weight Percent) | Yield of ADD (mg) | Remaining Substrate (mg) |
|---|---|---|---|---|
| 1 | Cholesterol | 0 | 4.7 | 53.2 |
| 2 | " | 0.15 | 5.2 | 45.3 |
| 3 | " | 0.3 | 12.6 | 25.3 |
| 4 | " | 0.5 | 15.7 | 18.7 |
| 5 | " | 0.7 | 18.8 | 7.5 |
| 6 | " | 1.0 | 25.8 | 0 |
| 7 | " | 1.5 | 27.2 | 0 |
| 8 | " | 2.5 | 20.8 | 2.2 |
| 9 | " | 3.0 | 16.4 | 10.2 |
| 10 | " | 3.5 | 13.5 | 12.8 |
| 11 | " | 4.0 | 10.0 | 13.6 |
| 12 | Sitosterol + Campesterol (2:1) | 0 | 2.0 | 75.0 |
| 13 | " | 0.3 | 6.8 | 50.0 |
| 14 | " | 0.5 | 6.9 | 48.8 |
| 15 | " | 1.5 | 9.7 | 35.8 |
| 16 | Stigmasterol | 0 | 1.0 | 88.8 |
| 17 | " | 1.5 | 4.2 | 50.3 |
| 18 | Cholest-4-en-3-one | 0 | 8.4 | 17.5 |
| 19 | " | 1.5 | 21.3 | 8.5 |
| 20 | Cholesta-1,4-dien-3-one | 0 | 6.9 | 12.6 |
| 21 | " | 1.5 | 15.5 | 10.8 |

EXAMPLE 2

This Example illustrates the increased yield of ADD by the addition of the fat to the culture medium.

A medium having the following composition is prepared:
- 2.0 percent of sucrose,
- 1.0 percent of $NaNO_3$,
- 1.0 percent of yeast extract,
- 0.25 percent of $K_2HPO_4$,
- 0.03 percent of $MgSO_4 \cdot 7H_2O$,
- an amount of the fat to effect the concentration indicated in Table 2, and remainder - water The pH of the medium is adjusted to 7.0 with NaOH. To a 500 ml shaker flask is added 50 ml of the medium. The flask and its contents are sterilized by autoclaving for a period of 10 minutes at a temperature of 120° C, and then cooled. The flask is inoculated with 1 ml of the seed culture broth which is obtained by the same procedure as in Example 1 with the exception that *Brevibacterium lipolyticum* (IAM 1398) is used instead of *Arthrobacter simplex* (IAM 1660). The inoculated medium is incubated at a temperature of 30° C on a reciprocal shaker the same as that described in Example 1. At the end of 15 hours from the time of initiating the incubation, 200 mg of cholesterol is added to the medium. At the end of 28 hours from the time of initiating the incubation, 1.0 mg of 1,10-phenanthroline is added. The incubation is continued for an additional 70 hours. At the end of this period, the products are extracted with ethyl acetate and separated in the same manner as in Example 1. The yield of ADD is shown in Table 2.

TABLE 2

| Run No. | Fat | Concentration (weight percent) | Yield of ADD (mg) |
|---|---|---|---|
| 1 | None | 0 | 12 |
| 2 | Soybean oil | 0.15 | 15 |
| 3 | " | 0.3 | 20 |
| 4 | " | 0.5 | 37 |
| 5 | " | 1.0 | 39 |
| 6 | " | 2.0 | 41 |
| 7 | " | 3.0 | 25 |
| 8 | " | 4.0 | 15 |
| 9 | Soya lecithin | 1.0 | 38 |
| 10 | " | 2.0 | 38 |
| 11 | " | 3.0 | 30 |
| 12 | " | 4.0 | 18 |
| 13 | Peanut oil | 2.0 | 40 |
| 14 | Sesame oil | 2.0 | 30 |
| 15 | Olive oil | 2.0 | 32 |
| 16 | Corn oil | 2.0 | 33 |
| 17 | Rapeseed oil | 2.0 | 38 |
| 18 | Rice bran oil | 2.0 | 35 |
| 19 | Palm oil | 2.0 | 35 |
| 20 | Coconut oil | 2.0 | 36 |
| 21 | Cottonseed oil | 2.0 | 40 |
| 22 | Crude soybean oil | 2.0 | 32 |
| 23 | Lard | 2.0 | 29 |
| 24 | Whale oil | 2.0 | 32 |
| 25 | Castor oil | 2.0 | 38 |
| 26 | Soybean oil plus Castor oil | 2.0 0.3 | 43 |

EXAMPLE 3

This Example illustrates an increase in the yield of ADD by the addition of the glyceride to the culture medium. Example 2 is repeated except that 3.0 mg of 8-hydroxyquinoline is used in place of 1,10-phenanthroline, and that in place of the fat, an amount of the glyceride is added to effect the concentration shown in Table 3, and that the incubation is stopped at the end of 28 hours from the time of the addition of 8-hydroxyquinoline (at the end of 56 hours from the time of the addition of 8-hydroxyquinoline). When the incubation is stopped at this early stage, DHT is formed along with ADD. Upon completion of the incubation, the fermentation broth is treated in the same manner as in Example 1.

The results are shown in Table 3.

TABLE 3

| Run No. | Glyceride | Concentration (weight percent) | Yield ADD (mg) | Yield DHT (mg) |
|---|---|---|---|---|
| 1 | None | 0 | 14 | 2 |
| 2 | Tristearin | 0.5 | 19 | 14 |
| 3 | " | 1.0 | 25 | 18 |
| 4 | " | 1.5 | 27 | 16 |
| 5 | " | 2.0 | 23 | 16 |
| 6 | " | 3.0 | 19 | 16 |
| 7 | " | 4.0 | 15 | 5 |
| 8 | Triolein | 1.5 | 21 | 25 |
| 9 | α-Monostearin | 1.5 | 27 | 18 |
| 10 | α, α'-Distearin | 1.5 | 20 | 14 |
| 11 | Tripalmitin | 1.5 | 26 | 16 |

The attached drawing illustrates the relationship between the incubation time, and the concentrations of cholesterol and the oxidation products thereof which are formed in Run 4 of this Example.

EXAMPLE 4

This Example illustrates the increased yield of ADD by the addition of rapeseed oil to the culture medium.

A seed medium having the following composition is prepared:
 2.0 percent of η-paraffin (main component $C_{14}$),
 0.5 percent of ammonium sulfate,
 0.25 percent of $K_2HPO_4$,
 0.1 percent of $MgSO_4.7H_2O$,
 0.5 percent of corn steep liquor, and remainder - water The pH of the seed medium is adjusted to 7.5 with NaOH. To a 500 ml shaker flask is added 100 ml of the seed medium. The flask and its contents are sterilized by autoclaving for a period of 15 minutes at a temperature of 120° C, and then cooled. The seed medium is inoculated with a loopful of *Nocardia erythropolis* (ATCC 4277) and the inoculated medium is incubated for a period of 35 hours at a temperature of 30° C on a reciprocal shaker similar to that described in Example 1.

A main fermentation medium having the following composition is prepared:
 1.0 percent of glucose
 0.5 percent of yeast extract
 0.5 percent of malt extract
 0.5 percent of meat extract
 0.1 percent of $K_2HPO_4$
 0.02 percent of $MgSO_4.7H_2O$
 1.0 percent of rapeseed oil The pH of the medium is adjusted to 7.0 with NaOH. To a 500 ml shaker flask is added 50 ml of the main fermentation medium. The flask and its contents are sterilized by autoclaving for a period of 20 minutes at a temperature of 120° C and then cooled. The flask is inoculated with 2 ml of the seed culture broth obtained above, and incubated at a temperature of 30° C on a reciprocal shaker similar to that described in Example 1. At the end of 20 hours from the time of initiating the main fermentation, 150 mg of cholesterol is added. At the end of 28 hours from the time of initiating the main fermentation, 4.7 mg of 2,2'-bipyridyl is added. At the end of 70 hours from the time of the addition of 2,2'-bipyridyl, the incubation is stopped. Upon completion of the incubation, the same treatment as in Example 1 gives 12 mg of ADD.

When the procedure described above is repeated with the exception that rapeseed oil is not added to the culture medium, 8 mg of ADD is obtained.

EXAMPLE 5

This Example illustrates the effect of the addition of rapeseed oil and soybean oil meal on the yield of ADD.

A seed medium having the following composition is prepared:
 1.0 percent of glucose,
 0.3 percent of meat extract,
 1.0 percent of peptone,
 0.5 percent of NaCl, and remainder - water The pH of the seed medium is adjusted to 7.2 with NaOH. To a 500 ml shaker flask is added 100 ml of the seed medium. The flask and its contents are sterilized by autoclaving for a period of 20 minutes at a temperature of 120° C and then cooled. The flask is inoculated with a loopful of *Mycobacterium phlei* (IFO 3158) and incubated for a period of 70 hours at a temperature of 35° C on a reciprocal shaker the same as that described in Example 1.

A main fermentation medium having the following composition is prepared:
 2.0 percent of corn steep liquor,
 2.0 percent of glucose,
 0.4 percent of sodium glutamate,
 0.2 percent of asparagine,
 0.2 percent of $KH_2PO_4$,
 1.0 percent of rapeseed oil, and remainder - water The pH of the medium is adjusted to 7.0 with NaOH. To a 500 ml shaker flask is added 50 ml of the main fermentation medium. The flask and its contents are sterilized by autoclaving for a period of 20 minutes at a temperature of 120° C and then cooled. The flask is inoculated with 2 ml of the seed culture broth obtained above, and incubated at a temperature of 35° C on a reciprocal shaker the same as that described in Example 1.

At the end of 40 hours from the time of initiating the main fermentation, 150 mg of cholesterol is added to the culture medium. At the end of 48 hours from the time of initiating the main fermentation, 6.2 mg of 2,2'-bipyridyl is added to the culture medium. At the end of 96 hours from the time of the addition of 2,2'-bipyridyl, the fermentation is stopped.

Upon completion of the fermentation, the same treatment as in Example 1 gives 25 mg of ADD.

When the procedure described above is repeated with the exception that 4.0 percent of soybean oil meal is present in the culture medium, 38 mg of ADD is obtained.

When the procedure described above is repeated with the exception that rapeseed oil is not added to the culture medium, 20 mg of ADD is obtained.

EXAMPLE 6

This Example illustrates an increase in yield of ADD by the addition of the fat and the vegetable oil meal, and by the addition of the ground oil seed.

Example 2 is repeated except that substances which are added to the culture medium are varied as indicated in Table 4, and that in place of 1,10-phenanthroline, 2,2'-bipyridyl is added in the amount listed in Table 4. The oil seeds which are used in this Example are ground in Waring Blender.

TABLE 4

| Run No. | Added Substance | Concentration (weight percent) | 2,2'-bipyridyl (mg) | Yield of ADD (mg) |
|---|---|---|---|---|
| 1 | None | 0 | 3.9 | 16 |
| 2 | Rapeseed oil | 1.0 | 3.9 | 35 |
| 3 | Rapeseed oil | 1.0 | | |
|   | Rapeseed oil meal | 2.0 | 5.5 | 50 |
| 4 | Ground Rapeseed | 2.5 | 5.5 | 45 |
| 5 | Linseed oil | 1.0 | 3.9 | 33 |
| 6 | Linseed oil | 1.0 | | |
|   | Linseed oil meal | 1.0 | 5.5 | 42 |
| 7 | Ground Linseed | 2.5 | 5.5 | 45 |
| 8 | Soybean oil | 1.0 | 3.9 | 33 |
| 9 | Soybean oil | 1.0 | | |
|   | Soybean oil meal | 1.0 | 5.5 | 49 |
| 10 | Ground soybean | 5.0 | 5.5 | 48 |
| 11 | Sesame oil | 1.0 | 3.9 | 37 |
| 12 | Sesame oil | 1.0 | | |
|   | Sesame oil meal | 2.0 | 5.5 | 45 |
| 13 | Ground sesame | 2.5 | 5.5 | 51 |

EXAMPLE 7

This Example illustrates the effect of the time of the addition of rapeseed oil on the yield of ADD.

A medium having the following composition is prepared:
  2.0 percent of sucrose,
  1.0 percent of NaNO$_3$,
  1.0 percent of yeast extract,
  0.25 percent of K$_2$HPO$_4$,
  0.03 percent of MgSO$_4$.7H$_2$O,
  3.0 percent of rapeseed oil, and remainder - water The pH of the medium is adjusted to 7.0 with NaOH. To a 500 ml shaker flask is added 50 ml of the medium. The flask and its contents are sterilized by autoclaving for a period of 10 minutes at a temperature of 120° C and then cooled. The flask is inoculated with 1 ml of the seed culture broth which is obtained in the same manner as in Example 2. The inoculated medium is incubated at a temperature of 30° C on a reciprocal shaker similar to that described in Example 1. At the end of 25 hours from the time of initiating the incubation, 250 mg of cholesterol is added. At the end of 30 hours from the time of initiating the incubation, 5.5 mg of 2,2'-bipyridyl is added. At the end of a period of time from the time of initiating the incubation as indicated in Table 5, 1.0 g of rapeseed oil is added to the culture medium. At the end of 110 hours from the time of initiating the incubation, the incubation is stopped. The formed ADD is separated in the same manner as in Example 1.

The procedure described above is repeated with the exception that the time of the addition of rapeseed oil is varied as indicated in Table 5.

TABLE 5

| Time of Addition of Rapeseed oil (hours) | Yield of ADD (mg) |
| --- | --- |
| 0 | 47 |
| 20 | 52 |
| 30 | 48 |
| 42 | 45 |
| 70 | 23 |
| 90 | 22 |
| no addition | 22 |

EXAMPLE 8

This Example illustrates the increased yield of ADD by the addition of the vegetable oil meal along with the fat to the culture medium. A seed medium having the following composition is prepared:
  1.0 percent of yeast extract,
  1.0 percent of meat extract,
  1.0 percent of peptone, and remainder - water The pH of the seed medium is adjusted to 7.0 with NaOH. To a 500 ml shaker flask is added 100 ml of the seed medium. The flask and its contents are sterilized by autoclaving for a period of 15 minutes at a temperature of 120° C, and then cooled. The medium is inoculated with a loopful of *Arthrobacter simplex* (IAM 1660) and the inoculated medium is incubated for a period of about 48 hours at a temperature of 28 C on a reciprocal shaker similar to that described in Example 1.

A main fermentation medium having the same composition as that of the seed medium with the exception that the required amounts of the fat and the vegetable oil meal shown in Table 6 are added to the medium to achieve the listed concentrations.

The pH of the main fermentation medium is adjusted to 7.0 with NaOH. To a 500 ml shaker flask is added 50 ml of the main fermentation medium. The flask and its contents are sterilized by autoclaving for a period of 20 minutes at a temperature of 120° C, and then cooled. The flask is inoculated with 2 ml of the seed culture broth obtained above and then placed on a reciprocal shaker having a 7-cm stroke. The main fermentation is initiated at a temperature of 30° C. At the end of 20 hours from the time of initiating the incubation, 150 mg of cholesterol suspended in 2 ml of water is added. At the end of 28 hours from the time of initiating the incubation, 6.2 mg of 2,2'-bipyridyl is added. At the end of 85 hours from the time of the addition of 2,2'-bipyridyl, the incubation is stopped. The fermentation broth is extracted with 150 ml of ethyl acetate. The extract is concentrated, chromatographed on silica gel and eluted with benzene-acetone (1:1), thereby separating ADD from intermediate oxidation products and the steroid substrate. The yield of ADD is shown in Table 6.

Employing a mixture of β-sitosterol and campesterol (2:1), stigmasterol, cholest-4-en-3-one or cholesta-1,4-dien-3-one in place of cholesterol, the above-described incubation is repeated.

In addition, the above-described incubation is repeated except that the fat and the vegetable oil meal are not added to the culture medium.

The results are shown together in Table 6.

TABLE 6

| Run No. | Substrate | Fats and Vegetable oil meals | Concentration (weight percent) | Yield of ADD (mg) | Remaining Substrate (mg) |
| --- | --- | --- | --- | --- | --- |
| 1 | Cholesterol | None | 0 | 3 | 53 |
| 2 | " | Linseed oil | 1.0 | 26 | 0 |
| 3 | " | Linseed oil meal | 2.0 | 18 | 0 |
| 4 | " | Linseed oil | 1.0 | | |
| | | Linseed oil meal | 2.0 | 55 | 0 |
| 5 | " | Sesame oil | 1.0 | 29 | 0 |
| 6 | " | Sesame oil meal | 2.0 | 20 | 0 |
| 7 | " | Sesame oil | 1.0 | 52 | 0 |
| | | Sesame oil meal | 2.0 | | |
| 8 | Sitosterol-Campesterol (2:1) | None | 0 | 2 | 70 |
| 9 | " | Linseed oil | 1.0 | 10 | 40 |
| 10 | " | Linseed oil meal | 2.0 | 7 | 58 |
| 11 | " | Linseed oil | 1.0 | | |
| | | Linseed oil meal | 2.0 | 20 | 22 |
| 12 | Stigmasterol | None | 0 | 1 | 86 |
| 13 | Stigmasterol | Linseed oil | 1.0 | 4 | 50 |
| 14 | " | Linseed oil meal | 2.0 | 4 | 50 |
| 15 | " | Linseed oil | 1.0 | 9 | 38 |
| | | Linseed oil meal | 2.0 | | |
| 16 | Cholest-4-en-3-one | None | 0 | 5 | 18 |
| 17 | " | Linseed oil | 1.0 | 23 | 4 |
| 18 | " | Linseed oil | 1.0 | 55 | 0 |
| | | Linseed oil meal | 2.0 | | |
| 19 | Cholesta-1,4-dien-3-one | None | 0 | 5 | 13 |
| 20 | " | Linseed oil | 1.0 | 22 | 0 |
| 21 | " | Linseed oil | 1.0 | 53 | 0 |
| | | Linseed oil meal | 2.0 | | |

EXAMPLE 9

This Example illustrates the effect of the amounts of soybean oil and soybean oil meal to be added on the yield of ADD.

The procedure of Example 8 is repeated with following changes in amounts of the substances which are added to the culture medium:

(1) 200 mg of cholesterol is used as a substrate.
(2) Soybean oil and soybean oil meal are added in amounts required to give the concentrations as indicated in Table 7.
(3) When more than 8 percent of soybean oil meal is present in the culture medium, 7.8 mg of 2,2'-bipyridyl is added.

The results are shown in Table 7.

TABLE 7

| Run No. | Soybean oil (weight percent) | Soybean oil meal (weight percent) | Yield of ADD (mg) |
| --- | --- | --- | --- |
| 1 | 0 | 0 | 3 |
| 2 | 0 | 2.5 | 15 |
| 3 | 0.15 | 2.5 | 15 |
| 4 | 0.25 | 1.5 | 13 |
| 5 | 0.25 | 2.5 | 16 |
| 6 | 0.30 | 2.5 | 29 |
| 7 | 0.50 | 2.5 | 41 |
| 8 | 0.50 | 5.0 | 48 |
| 9 | 0.50 | 8.0 | 51 |
| 10 | 0.50 | 10.0 | 43 |
| 11 | 0.50 | 15.0 | 38 |
| 12 | 0.50 | 20.0 | 22 |
| 13 | 1.0 | 0 | 36 |
| 14 | 1.0 | 0.3 | 45 |
| 15 | 1.0 | 0.6 | 51 |
| 16 | 1.0 | 1.0 | 54 |
| 17 | 1.0 | 2.5 | 53 |
| 18 | 1.0 | 5.0 | 54 |
| 19 | 1.0 | 8.0 | 52 |
| 20 | 1.0 | 10.0 | 47 |
| 21 | 1.0 | 15.0 | 36 |
| 22 | 1.5 | 2.5 | 50 |
| 23 | 3.0 | 0 | 25 |
| 24 | 3.0 | 0.1 | 26 |
| 25 | 3.0 | 0.3 | 36 |
| 26 | 3.0 | 0.9 | 45 |
| 27 | 3.0 | 1.8 | 47 |
| 28 | 3.0 | 2.5 | 48 |
| 29 | 3.5 | 2.5 | 45 |
| 30 | 4.0 | 2.5 | 20 |
| 31 | 6.0 | 2.5 | 8 |

EXAMPLE 10

This Example illustrates the effect of the addition of the fat and the vegetable oil meal on the yield of ADD. A medium having the following composition is prepared:

2.0 percent of sucrose,
1.0 percent of $NaNO_3$,
1.0 percent of yeast extract,
0.25 percent of $K_2HPO_4$,
0.03 percent of $MgSO_4 \cdot 7H_2O$, amounts of the fat and the vegetable oil meal to give the concentration indicated in Table 8, and remainder - water The pH of the medium is adjusted to 7.0 with NaOH. To a 500 ml shaker flask is added 50 ml of the medium. The flask and its contents are sterilized by autoclaving for a period of 20 minutes at a temperature of 120° C and then cooled. The flask is inoculated with 1 ml of the seed culture broth which is obtained in the same manner as in Example 8 with the exception that *Brevibacterium Lipolyticum* (IAM 1398) is employed in place of *Arthrobacter simplex* (IAM 1660).

The inoculated medium is incubated at a temperature of 30° C on a reciprocal shaker the same as that described in Example 1. At the end of 15 hours from the time of initiating the incubation, 200 mg of cholesterol is added. At the end of 28 hours from the time of initiating the incubation, the amount of 2,2'-bipyridyl shown in Table 8 is added and then the fermentation is continued for an additional 70 hours. At the end of this period, the products are extracted with ethyl acetate and separated in the same manner as in Example 8. The yield of ADD is shown in Table 8.

TABLE 8

| Run No. | Fats and Vegetable oil meals | Concentration (weight percent) | 2,2'-Bipyridyl (mg) | Yield of ADD (mg) |
| --- | --- | --- | --- | --- |
| 1 | None | 0 | 3.9 | 16 |
| 2 | Rapeseed oil | 1.0 | 3.9 | 35 |
| 3 | Rapeseed oil | 1.0 | | |
| | Rapeseed oil meal | 2.0 | 5.5 | 50 |
| 4 | Linseed oil | 1.0 | 3.9 | 33 |
| 5 | Linseed oil | 1.0 | | |
| | Linseed oil meal | 2.0 | 5.5 | 42 |
| 6 | Soybean oil | 1.0 | 3.9 | 35 |
| 7 | Soybean oil | 1.0 | 5.5 | 49 |
| | Soybean oil meal | 2.0 | | |
| 8 | Sesame oil | 1.0 | 3.9 | 37 |
| 9 | Sesame oil | 1.0 | 5.5 | 45 |
| | Sesame oil meal | 2.0 | | |
| 10 | Cottonseed oil | 1.0 | 3.9 | 32 |
| 11 | Cottonseed oil | 1.0 | 5.5 | 40 |
| | Cottonseed meal | 2.0 | | |
| 12 | Peanut oil | 1.0 | 3.9 | 37 |
| 13 | Peanut oil | 1.0 | 5.5 | 50 |
| | Peanut oil meal | 2.0 | | |

EXAMPLE 11

This Example illustrates the effect of the addition of the glyceride-containing substance and the vegetable oil meal on the yields of DHT and ADD. Example 10 is repeated except that the substances which are added to the culture medium are varied as indicated in Table 9, and that the amount of 1,10-phenanthroline indicated in Table 9 is used in place of 2,2'-bipyridyl, and that the incubation is stopped at the end of 28 hours from the time of initiating the incubation (at the end of 56 hours from the time of initiating the incubation).

When the incubation is stopped at this early stage, DHT is formed along with ADD. The yields of DHT and ADD are shown in Table 9.

TABLE 9

| Run No. | Added Substances | Concentration (weight percent) | 1,10-Phenanthroline (mg) | Yield ADD (mg) | Yield DHT (mg) |
| --- | --- | --- | --- | --- | --- |
| 1 | None | 0 | 1.3 | 7 | 4 |
| 2 | Triolein | 1.0 | | | |
| | Linseed oil meal | 2.0 | 1.3 | 24 | 25 |
| 3 | Triolein | 1.0 | | | |
| | Soybean oil meal | 2.0 | 1.3 | 22 | 25 |
| 4 | Triolein | 1.0 | | | |
| | Sesame oil meal | 2.0 | 1.3 | 25 | 23 |
| 5 | Triolein | 1.0 | | | |
| | Rapeseed oil meal | 2.0 | 1.3 | 21 | 28 |
| 6 | α-Monopalmitin | | | | |
| | Sesame oil meal | 2.0 | 1.0 | 23 | 21 |
| 7 | α-Monopalmitin | 1.0 | | | |
| | Peanut oil meal | 2.0 | 1.3 | 21 | 17 |
| 8 | α-Monopalmitin | 1.0 | | | |
| | Cottonseed meal | 2.0 | 1.3 | 19 | 21 |
| 9 | α-Monopalmitin | 1.0 | | | |
| | Soybean oil meal | 2.0 | 1.3 | 19 | 23 |
| 10 | Palm oil | 0.25 | | | |
| | Rapeseed oil meal | 2.0 | 1.3 | 7 | 7 |
| 11 | Palm oil | 0.3 | | | |
| | Rapeseed oil meal | 2.0 | 1.3 | 13 | 10 |
| 12 | Palm oil | 0.5 | | | |
| | Rapeseed oil meal | 2.0 | 1.3 | 16 | 13 |
| 13 | Palm oil | 1.0 | | | |
| | Rapeseed oil meal | 0.3 | 1.3 | 18 | 10 |
| 14 | Palm oil | 1.0 | | | |
| | Rapeseed oil meal | 0.6 | 1.3 | 18 | 14 |
| 15 | Palm oil | 1.0 | | | |
| | Rapeseed oil meal | 1.0 | 1.3 | 20 | 20 |

TABLE 9-continued

| Run No. | Added Substances | Concentration (weight percent) | 1,10-Phenanthroline (mg) | Yield ADD (mg) | Yield DHT (mg) |
|---|---|---|---|---|---|
| 16 | Palm oil | 1.0 | | | |
| | Rapeseed oil meal | 2.0 | 1.3 | 22 | 24 |
| 17 | Palm oil | 1.0 | | | |
| | Rapeseed oil meal | 5.0 | 1.3 | 22 | 26 |
| 18 | Palm oil | 1.0 | | | |
| | Rapeseed oil meal | 10.0 | 1.6 | 21 | 20 |
| 19 | Palm oil | 1.0 | | | |
| | Rapeseed oil meal | 15.0 | 1.6 | 18 | 17 |
| 20 | Palm oil | 1.0 | | | |
| | Rapeseed oil meal | 20.0 | 1.6 | 15 | 12 |
| 21 | Lard | 1.0 | | | |
| | Sesame oil meal | 2.0 | 1.3 | 20 | 28 |
| 22 | Lard | 10.0 | 1.3 | 22 | 23 |
| | Cottonseed meal | 2.0 | | | |

EXAMPLE 12

This Example illustrates the effect of the simultaneous addition of the fat and the vegetable oil meal on the yield of ADD.

A medium having the following composition is prepared:
2.0 percent of corn steep liquor,
2.0 percent of glucose,
0.4 percent of sodium glutamate,
0.2 percent of asparagine,
0.2 percent of $KH_2PO_4$,
amounts of the fat and the vegetable oil meal to achieve the concentration listed in Table 10, and
remainder - water The pH of the medium is adjusted to 7.0 by the addition of NaOH. To a 500 ml shaker flask is added 50 ml of the medium. The flask and its contents are sterilized by autoclaving for a period of 20 minutes at a temperature of 120° C. The flask is inoculated with 2 ml of the seed culture broth which is obtained in the same manner as in Example 5. The inoculated medium is incubated at a temperature of 35° C on a reciprocal shaker similar to that described in Example 1. At the end of 40 hours from the time of initiating the incubation, 150 mg of cholesterol is added to the medium. At the end of 48 hours from the time of initiating the incubation, 4.2 mg of 8-hydroxyquinoline is added to the medium. At the end of 60 hours from the time of the addition of 8-hydroxyquinoline, the fermentation is terminated. Upon completion of the fermentation, the formed ADD is recovered from the fermentation broth by the same procedure as described in Example 1. The yield of ADD is shown in Table 10.

TABLE 10

| Run No. | Fat and Vegetable oil meal | Concentration (weight percent) | Yield of ADD (mg) |
|---|---|---|---|
| 1 | None | 0 | 12 |
| 2 | Linseed oil | 0.5 | |
| | Linseed oil meal | 2.0 | 26 |
| 3 | Rapeseed oil | 0.5 | |
| | Rapeseed oil meal | 2.0 | 33 |
| 4 | Cottonseed oil | 0.5 | 27 |
| | Cottonseed meal | 2.0 | |
| 5 | Cottonseed oil | 0.5 | |
| | Sesame oil meal | 2.0 | 32 |
| 6 | Cottonseed oil | 0.5 | |
| | Peanut oil meal | 2.0 | 24 |
| 7 | Cottonseed oil | 0.5 | |
| | Soybean oil meal | 2.0 | 37 |
| 8 | Soybean oil | 0.5 | |
| | Soybean oil meal | 1.0 | 22 |
| 9 | Soybean oil | 0.5 | |

TABLE 10-continued

| Run No. | Fat and Vegetable oil meal | Concentration (weight percent) | Yield of ADD (mg) |
|---|---|---|---|
| | Soybean oil meal | 2.0 | 35 |
| 10 | Soybean oil | 0.5 | |
| | Soybean oil meal | 5.0 | 38 |
| 11 | Soybean oil | 0.5 | |
| | Soybean oil meal | 8.0 | 26 |
| 12 | Soybean oil | 0.5 | 19 |
| | Soybean oil meal | 10.0 | |

EXAMPLE 13

This Example also illustrates the effect of the addition of the fat and the vegetable oil meal on the yield of ADD. A medium having the following composition is prepared:
2.0 percent of corn steep liquor,
2.0 percent of glucose,
0.4 percent of sodium glutamate,
0.2 percent of asparagine,
0.2 percent of $KH_2PO_4$,
amounts of the fat and the vegetable oil meal to effect the concentration listed in Table 11, and
remainder - water The pH of the medium is adjusted to 7.0 by the addition of NaOH. To a 500 ml shaker flask is added 50 ml of the medium. The flask and its contents are sterilized by autoclaving for 20 minutes at 120° C. The flask is inoculated with 2 ml of the seed culture broth which is obtained by the same procedure as in Example 5 with the exception that *Protaminobacter alboflavus* (ATCC 8458) is employed as a microorganism, and that the seed incubation is carried out for 50 hours at 30° C. The inoculated medium is incubated at 30° C on the same shaker as in Example 1. At the end of 25 hours from the time of initiating the incubation, 200 mg of cholesterol is added. At the end of 33 hours from the time of initiating the incubation, 6.2 mg of 2,2'-bipyridyl is added. At the end of 95 hours from the time of initiating the incubation, the incubation is stopped. Upon completion of the incubation, the formed ADD is recovered from the fermentation broth by the same procedure as described in Example 1. The yield of ADD is shown in Table 11.

TABLE 11

| Run No. | Fat and Vegetable oil meal | Concentration (weight percent) | Yield of ADD (mg) |
|---|---|---|---|
| 1 | None | 0 | 4 |
| 2 | Soybean oil | 0.5 | 6 |
| 3 | Rapeseed oil | 0.5 | 6 |
| 4 | Soybean oil meal | 3.0 | 9 |
| 5 | Rapeseed oil meal | 3.0 | 9 |
| 6 | Soybean oil | 0.5 | |
| | Soybean oil meal | 3.0 | 12 |
| 7 | Rapeseed oil | 0.5 | |
| | Rapeseed oil meal | 3.0 | 13 |

Having now fully described the invention, it will be apparent to one of ordinary skill in the art that many changes and modifications can be made thereto without departing from the spirit or scope of the invention as set forth herein.

What is claimed as new and desired to be secured by letters patent of the United State is:

1. In a process for the production of 17-hydroxyandrosta-1, 4-dien-3-one and/or androsta-1,4-diene-3,17-dione by fermenting a sterol, its 4-en-3-one sterol derivative or its 1,4-dien-3-one sterol derivative in a culture medium with a microorganism capable of microbiologically oxidizing said sterol or its derivatives to produce 17-hydroxyandrosta-1, 4-dien-3-one and/or androsta-1,4-dien-3,17-dione, the improvement which comprises adding to the culture medium at least one glyceride-containing substance selected from the group consisting of glycerides, fats, oil seeds and oil fruits in an amount sufficient that the culture medium contains at least 0.3 percent by weight of glycerides.

2. The process of claim 1 wherein the sterol is selected from the group consisting of cholesterol, stigmasterol, campesterol, sitosterol, ergosterol, brassicasterol and fucosterol.

3. The process of claim 2 wherein the sterol is selected from the group consisting of cholesterol, stigmasterol, campesterol and sitosterol.

4. The process of claim 1 wherein the microorganism belongs to the geneus selected from the group consisting of *Arthrobacter, Nocardia, Fusarium, Microbacterium, Mycobacterium, Protaminobacter, Brevibacterium, Corynebacterium, Bacillus, Serratia, Azotobacter, Streptomyces, Alkaligenes* and *Pseudomonas.*

5. The process of claim 4 wherein the microorganism is selected from the group consisting of *Arthrobacter simplex, Brevibacterium lipolyticum, Mycobacterium smegmatis, Protaminobacter alboflavus, Nocardia erythropolis, Corynebacterium equi* and *Mycobacterium phlei.*

6. The process of claim 5 wherein the microorganism is *Arthrobacter simplex* or *Brevibacterium lipolyticum.*

7. The process of claim 1 wherein the glyceride is selected from the group consisting of monoglycerides, diglycerides and triglycerides.

8. The process of claim 1 wherein the glyceride is a single glyceride or a mixed glyceride.

9. The process of claim 1 wherein the fat is selected from the group consisting of linseed oil, perilla oil, tung oil, sesame oil, corn oil, rapeseed oil, cottonseed oil, safflower oil, soybean oil, camellia oil, rice bran oil, olive oil, castor oil, peanut oil, coconut oil, palm oil, palm kernel oil, fish oil, whale oil, beef tallow, lard, mutton tallow, beef foot oil and liver oil.

10. The process of claim 1 wherein the oil seed and oil fruit are selected from the group consisting of linseed, olive, sesame, rapeseed, cottonseed, soybean, peanut and rice bran.

11. The process of claim 1 wherein the culture medium contains from 0.3 to 4.0 percent by weight of glycerides.

12. The process of claim 11 wherein the culture medium contains from 0.5 to 3.5 percent by weight of glycerides.

13. The process of claim 12 wherein the culture medium contains from 0.7 to 3.0 percent by weight of glycerides.

14. The process of claim 1 wherein additionally a vegetable oil meal is added to the culture medium.

15. The process of claim 14 wherein the amount of the vegetable oil meal to be added is from 0.1 to 50 times the weight of the glyceride-containing substance, and the concentration of the vegetable oil meal in the culture medium is from 0.3 to 15 percent by weight.

16. The process of claim 15 wherein the amount of the vegetable oil meal to be added is from 0.3 to 30 times the weight of the glyceride-containing substance, and the concentration of the vegetable oil meal in the culture medium is from 0.6 to 10 percent by weight.

17. The process of claim 16 wherein the amount of the vegetable oil meal to be added is from 0.6 to 20 times the weight of the glyceride-containing substance, and the concentration of the vegetable oil meal in the culture medium is from 1 to 8 percent by weight.

18. The process of claim 14 wherein the vegetable oil meal is selected from the group consisting of soybean oil meal, linseed oil meal, rapeseed oil meal, cotton seed meal, sesame oil meal, peanut oil meal and safflower oil meal.

19. In a process for the production of 17-hydroxyandrosta-1,4-dien-3-one and/or androsta-1,4-diene-3,17-dione by fermenting a sterol selected from the group consisting of cholesterol, stigmasterol, campesterol and sitosterol; its 4-en-3-one sterol derivative or its 1,4-dien-3-one sterol derivative in a culture medium with a microorganism selected from the group consisting of *Arthrobacter simplex,* and *Brevibacterium lipolyticum,* the improvement which comprises adding to the culture medium at least one glyceride-containing substance selected from the group consisting of glycerides, fats, oil seeds and oil fruits in an amount sufficient that the culture medium contains from 0.7 to 3.0 percent by weight of glycerides, and an amount of a vegetable oil meal which is from 0.6 to 20 times the weight of the glyceride-containing substance to give the concentration of the vegetable oil meal in the culture medium in the range of from 1 to 8 percent by weight.

* * * * *